United States Patent [19]

Steppe

[11] Patent Number: 5,106,366
[45] Date of Patent: Apr. 21, 1992

[54] MEDICAL FLUID CASSETTE AND CONTROL SYSTEM

[75] Inventor: Dennis L. Steppe, Anaheim, Calif.
[73] Assignee: Nestle, S.A., Switzerland
[21] Appl. No.: 490,438
[22] Filed: Mar. 8, 1990
[51] Int. Cl.$^5$ .............................................. A61M 1/00
[52] U.S. Cl. ......................................... 604/30; 604/34; 604/35; 604/118; 417/476
[58] Field of Search ................ 604/27, 30, 31, 34–35, 604/118, 119, 153, 317, 319, 320; 417/475–477

[56] References Cited

U.S. PATENT DOCUMENTS

| | | |
|---|---|---|
| 4,197,947 | 4/1980 | Zaidi . |
| 4,332,322 | 6/1982 | Jaeschke et al. . |
| 4,425,116 | 1/1984 | Bilstad et al. ............... 604/34 |
| 4,479,761 | 10/1984 | Bilstad et al. . |
| 4,493,695 | 1/1985 | Cook . |
| 4,523,679 | 6/1985 | Paikoff et al. . |
| 4,537,305 | 8/1985 | Takanashi . |
| 4,545,783 | 10/1985 | Vaughan . |
| 4,627,833 | 12/1986 | Cook . |
| 4,713,051 | 12/1987 | Steppe et al. . |
| 4,735,610 | 4/1988 | Akkas et al. . |
| 4,736,850 | 4/1988 | Bowman et al. . |
| 4,798,580 | 1/1989 | Demeo et al. . |
| 4,963,131 | 10/1990 | Wortrich ............... 604/34 |

Primary Examiner—Stephen C. Pellegrino
Assistant Examiner—Michael Rafa
Attorney, Agent, or Firm—James Arno; Sally Yeager; Robert L. Price

[57] ABSTRACT

There is provided a medical fluid cassette made of thermoformed plastic material which cooperates with a medical control unit having retaining structure cooperable with the cassette to assist in controlling the flow of fluid through tubing associated with the cassette.

15 Claims, 6 Drawing Sheets

CLOSED POSITION

OPEN POSITION

MEDICAL FLUID CASSETTE AND CONTROL SYSTEM

BACKGROUND OF THE INVENTION

The present invention relates to an improved medical fluid cassette and a medical fluid control system including such cassette.

Medical fluid cassettes and fluid circuit elements adapted for use therewith interconnect medical surgical instruments (e.g. irrigating and aspirating handpieces) with control equipment so that the latter can control the flow of fluid to and from an instrument. When using typical medical cassettes and their fluid tubing in an operative environment, much care is taken for maintaining component sterility and for insuring their correct and reliable connections. In practice, a circulator and a scrub nurse assist in removing and setting up the fluid cassette and irrigation and aspiration tubing to the appropriate fixtures on the control equipment as well as the surgical instrument itself. There is, however, a desire to minimize handling of the tubing by the scrub nurse and circulator.

A number of known approaches exist for adapting medical cassettes to suitable control equipment. In commonly owned U.S. Pat. No. 4,713,051 there is disclosed a significant improvement in this field. Disclosed is an improved medical cassette in which much of the responsibility and reliability for the fluid connection is removed from human operators. This is because the specifics of the cassette construction and its geometry minimize the number of fluid transfer operations necessary for setting up the cassette to the control unit and instrument.

Cassettes like the foregoing present significant improvements over prior approaches in this area. While cassettes of this type are nonetheless successful, there is a continuing desire to improve their performance as well as to reduce the cost of their manufacture. In this regard, such a cassette generally cooperates with components in the control unit for selectively pumping and/or interrupting or occluding and/or otherwise controlling the flow of fluid through tubing segments. More specifically this cassette and others, such as described in U.S. Pat. Nos. 4,493,695; 4,627,833; 4,735,610 and 4,798,580 require the use of inherent rigid surfaces to cooperate with the tubing and console components, such as solenoid plungers and pumping assemblies, for effecting the desired fluid control. Such a cassette construction necessitates making it or significant portions thereof of rigid material. These construction factors add to the overall cost of the cassettes.

SUMMARY OF THE INVENTION

It is an object of the present invention to provide medical fluid cassettes and system which enhance the reliability and ease in setting up such cassettes as well as significantly minimizing the cost of the cassettes. Towards the above end, the present invention provides for a medical fluid cassette for use in conjunction with a medical control unit. The control unit is of the type having an operable assembly for controlling the flow of fluid to and from a surgical instrument at an operative site. The control unit is formed with a surface which is configured for supporting the cassette and the unit is provided with a movable cassette retaining member having a relatively rigid portion selectively cooperable with the cassette when the latter is supported on the supporting surface.

In an illustrated embodiment, the cassette comprises a supporting member which is sized and shaped to supportingly cooperate with the supporting surface of the control unit. Provision is made for fluid circuitry means being positioned and supported by the supporting member. The circuitry means is controllable for controlling fluid flow therethrough. This occurs because of cooperation of the circuitry means with operable assemblies of the control unit and the rigid portion of the retaining member.

In another illustrated embodiment of the present invention, provision is made for an improved system including a medical fluid cassette and a medical control unit. The control unit has an operable assembly for controlling fluid to and from a surgical instrument at an operative site. The control unit has a surface configured to support the cassette and a movable cassette retaining member having at least a relatively rigid portion which is selectively cooperable with the cassette when the latter is supported on the supporting surface. The cassette comprises a supporting member which is sized and shaped to supportingly cooperate with the supporting surface of the control unit. Fluid circuitry means are provided so as to be positioned and supported by the supporting member. The fluid circuitry means are controllable by the operable assembly of the control unit for controlling fluid flow therethrough when the rigid portion, the fluid circuitry means and the operable assembly cooperate with each other.

In another illustrated embodiment of the present invention, provision is made for an improved system comprising a medical fluid cassette for use in combination with a medical control unit. The control unit is arranged to control the flow of fluid to and from a surgical instrument at an operative site. In this embodiment, the control unit includes a vacuum assembly for aspirating body tissue and fluids from a surgical instrument and an irrigating assembly being operable for supplying irrigating fluid to the operative site. Included in the control unit is a supporting surface configured for supporting the fluid cassette and also including a movable cassette retaining member having rigid portions cooperable with the fluid cassette when the latter is supported on the supporting surface. The retaining member is effective for retaining the fluid cassette on the supporting surface. The fluid cassette includes a supporting member made of a thin-walled flexible material which is sized and shaped to coapt with the supporting surface. Provision is also made for fluid irrigating and aspirating means carrying fluids to and from the surgical instrument. The cassette includes means for holding the irrigating and aspirating means so as to be in cooperable relationship with the irrigating and vacuum assemblies of the control unit, respectively. When the cassette is supported on the supporting surface by the retaining member, the rigid portions provide reaction surfaces so that when the irrigating and aspirating assemblies selectively cooperate with the irrigating and aspirating means, fluid flow through the irrigating and aspirating means can be controlled.

Among the other objects and features of the present invention are the provision of an improved medical fluid cassette and system using the same; the provision of a medical fluid cassette made of an entirely flexible and low cost material; and, the provision of an inexpensive and disposable medical fluid cassette which facilitates easy set-up of the fluid tubing.

Still other objects and further scope of applicability of the present invention will become apparent from the detailed description to follow when taken into conjunction with the accompanying drawings in which like parts are designated by like reference numerals throughout the several views.

DETAILED DESCRIPTION

Figure 1:
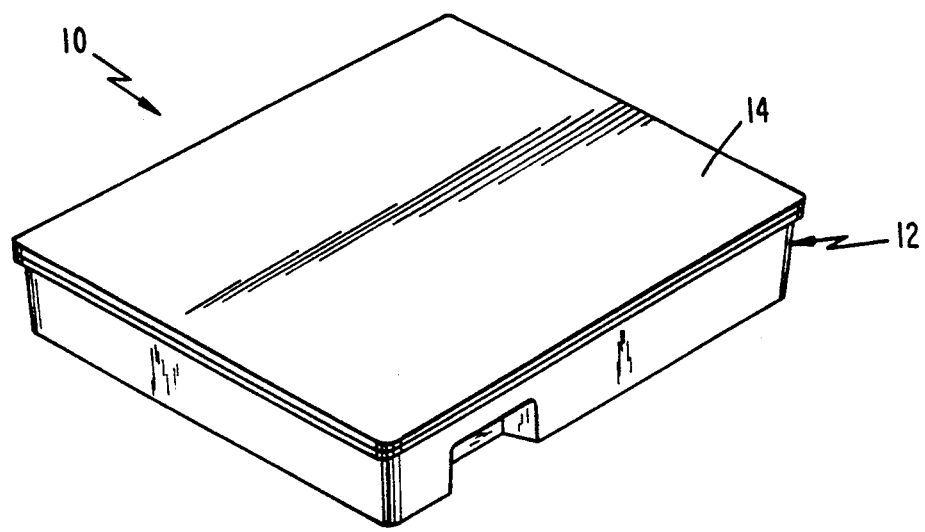
FIG. 1 is a perspective view of a thermoformed plastic fluid cassette of the present invention.
Figure 2:
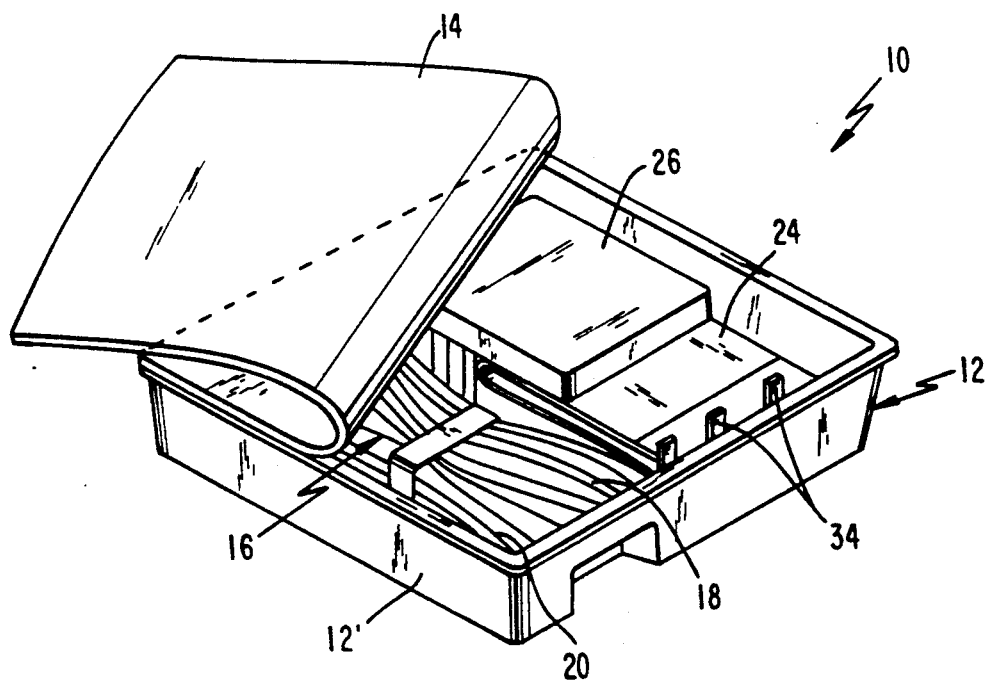
FIG. 2 is a perspective view of the fluid cassette with the lid thereof partially removed.
Figure 3:
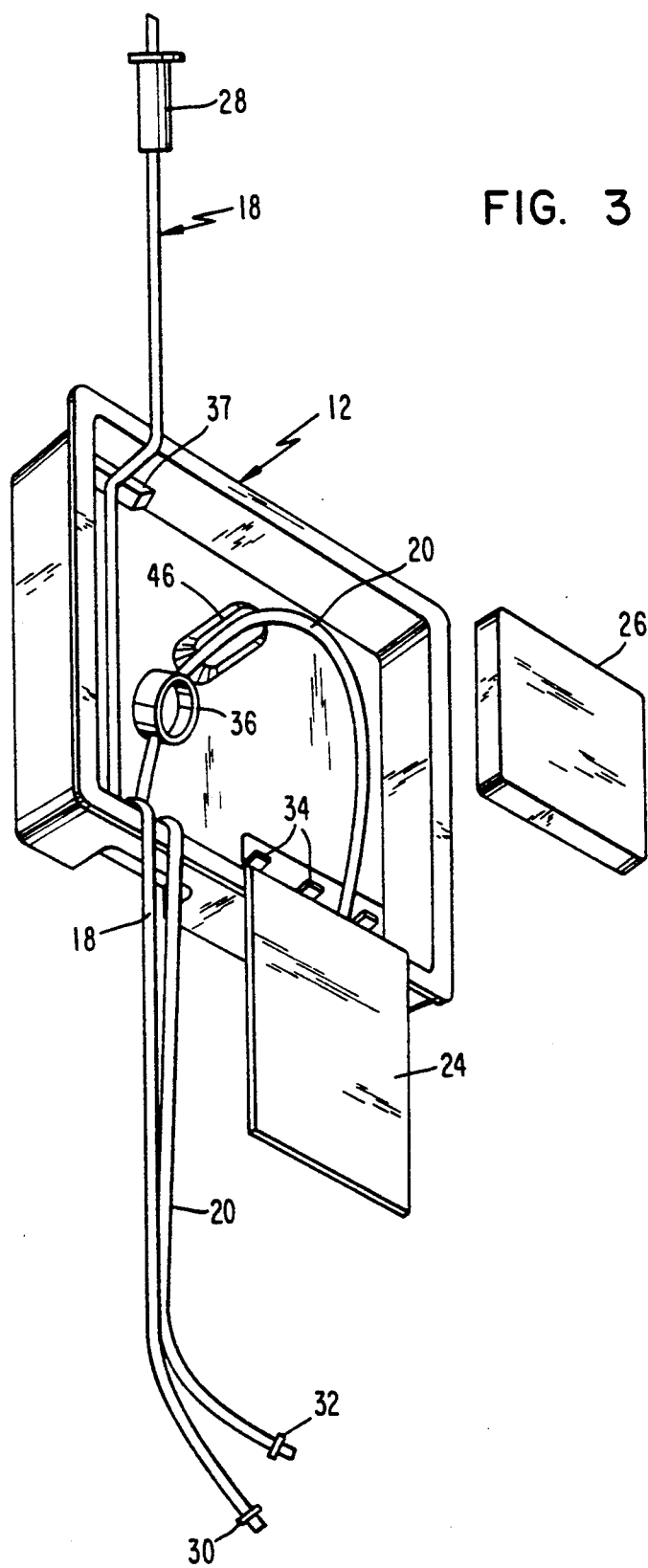
FIG. 3 is an exploded perspective view similar to FIG. 2, but with the cover completely removed and illustrating several medical and fluidic components.

Referring initially to FIGS. 1-3, there is illustrated a medical package 10 including a thermoformed plastic medical fluid housing or cassette 12 having a supporting body 12' in the configuration of a tray. The cassette 12 is sealed in a well-known way with a suitable peelable cover or lid 14. Sterilization of the package 10 is performed by suitable process. Following sterilization, the contents of the medical package 10 are sterile for shipping and storage purposes.

FIGS. 2 and 3 depict some of the contents of the medical fluid cassette 12. Included is a tubing set 16 comprising an inflow or irrigation tubing 18 and an outflow or aspiration tubing 20; a flexible debris container or drainage bag 24; and a storage container 26 which is intended to be removed from the cassette 12 and which includes accessories to be used in the surgical procedure. The irrigation and aspiration tubing members 18 and 20; respectively, are made of suitable material, such as silicone or PVC (i.e., polyvinylchloride) and are intended to extend in the manner shown in FIGS. 3 and 4.

The irrigation tubing 18 includes a drip chamber fitment 28 coupling to, for example, a gravity-feed irrigation assembly (not shown). Attached to the other end of the irrigation tubing member 18 is a male luer fitting 30 for releasable coupling to a suitable irrigating and aspirating handpiece (not shown) of the type which is well-known in the ophthalmological field. A female luer fitting 32 is attached to one end of the aspiration tubing member 20 for coupling to the irrigating and aspirating handpiece, while the other end is connected to the interior of the drainage bag 24. The drainage bag 24 is formed with a plurality of spaced openings which facilitate mounting thereof on a plurality of conically shaped and spaced apart protuberances or bosses 34. The bosses 34 extend outwardly and in an orientation so that the bag 24 can be suspended when in its normal operating condition.

Figure 9:
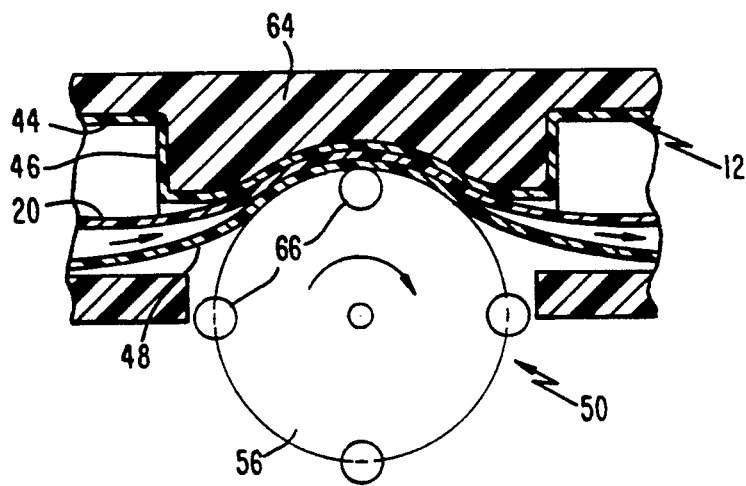

Fluidically interconnected to the aspiration tubing 20 is a vacuum control connector member 36. Formed integrally in the thermoformed walls of the fluid cassette body 12' is a plurality of clips 37, only one of which is shown in FIG. 3, which releasably secure and orient the tubing 18 and 20 in a predetermined fashion so they can easily cooperate with the appropriate electromechanical devices of a medical control unit 38 and irrigating and aspirating handpiece. Another clip similar to that depicted would be put in the opposite corner of the body. The fluid cassette body 12' includes an integral circular recess 40 (FIG. 4) formed on a bottom wall 44. The recess 40 is sized and shaped to hold the vacuum control connector 36 which is fluidically coupled to the aspiration tubing 20. Basically the vacuum control connector 36 allows venting of the aspiration line by the control unit 38 so as to control the vacuum in a known manner. In this embodiment, the vacuum control connector 36 is disc-shaped and includes a filter (not shown) therein. Also integrally formed by the walls of the fluid cassette 12 is a semi-circular shaped protuberance 46 (FIGS. 3 and 9). The protuberance 46 is formed with a groove that releasably holds an occludable segment 48 (FIG. 9) of the aspiration tubing 20 in a proper orientation for cooperation with a pumping assembly, generally designated by reference numeral 50 (FIG. 9).

Figure 4:
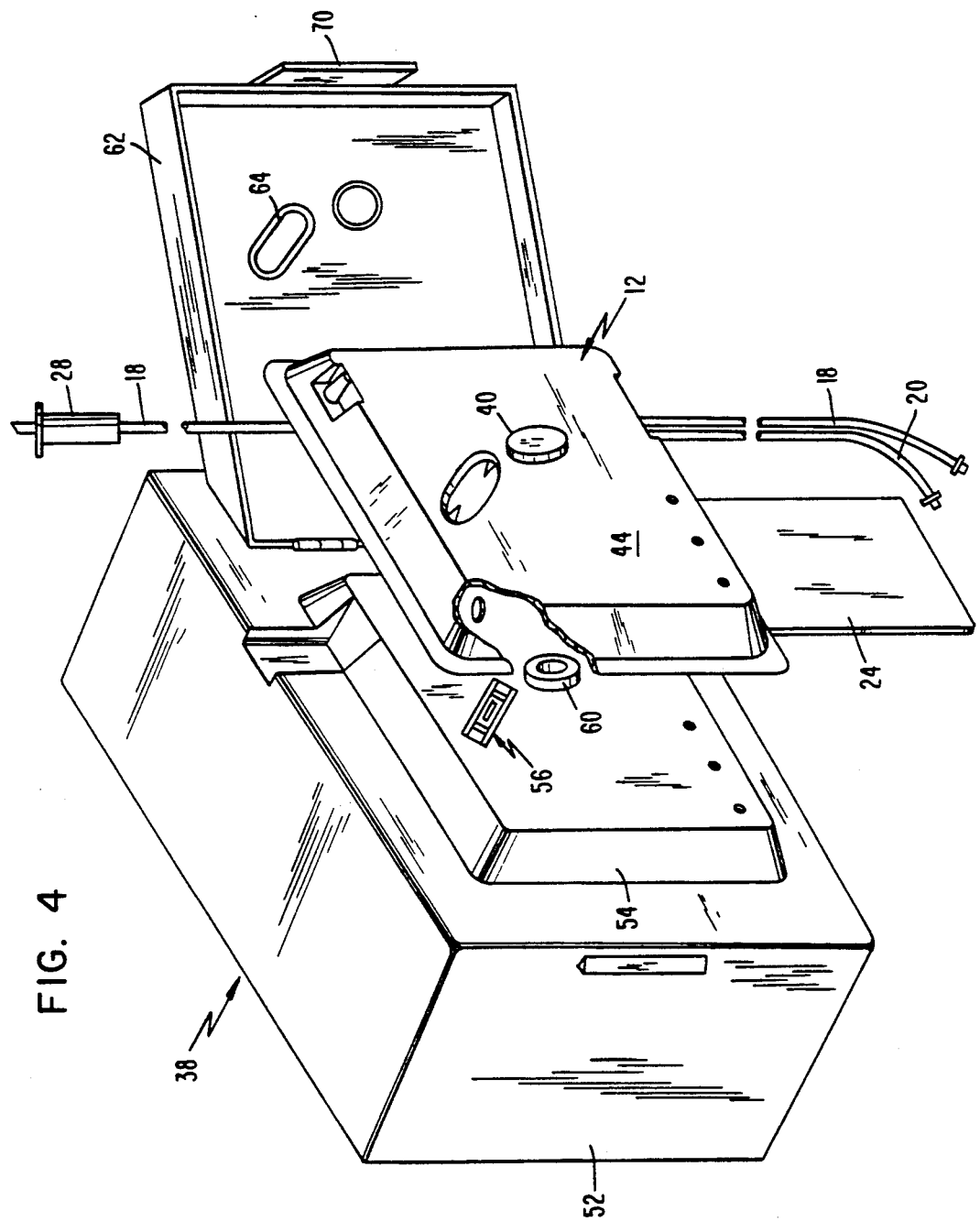
FIG. 4 is a perspective view of the fluid cassette and a control unit which cooperates with the former.
Figure 5:
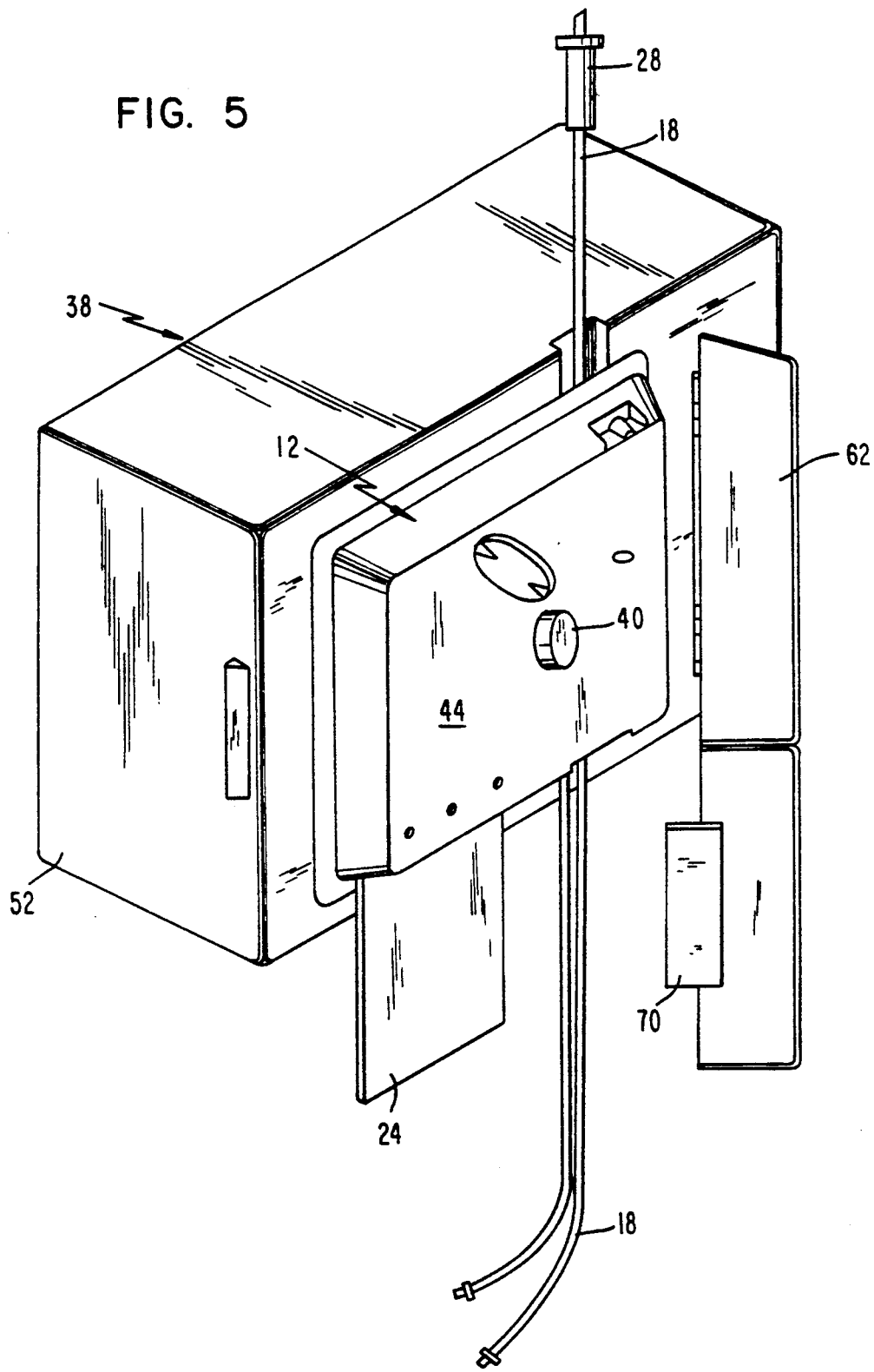
FIG. 5 is a perspective view of the fluid cassette attached to the control unit with a door attached to the control unit being shown in a partially closed position.
Figure 6:
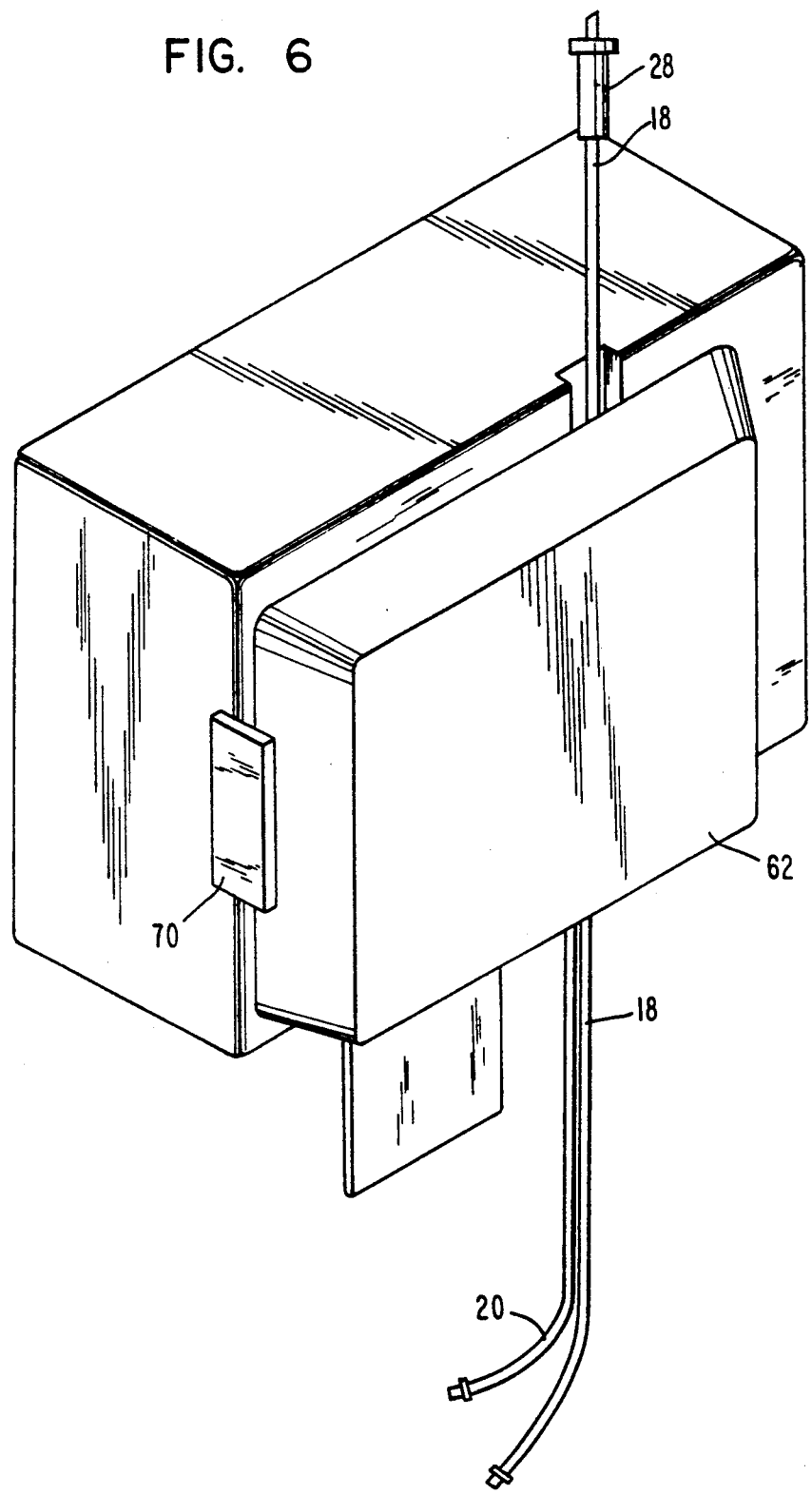
FIG. 6 is a perspective view like FIG. 5, but with the door in a closed position.
Figure 7:
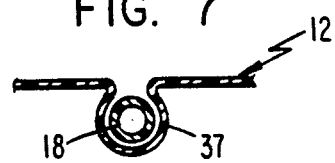
FIG. 7 is a cross-sectional view of a thermoformed clip portion retaining a segment of fluid tubing.

Reference is now made to FIGS. 4-6 for describing the medical control unit 38. Basically, the control unit 38 is of the type adapted for use in microsurgical situations, such as ophthalmic surgery, and controls irrigation and aspiration fluid flow to and from an irrigating and aspirating handpiece. It will be noted that only those aspects of the control unit 38 needed to understand the present invention will be set forth. The control unit 38 is formed with a generally parallelpiped housing 52. Extending laterally from the control unit housing 52 is a raised and generally rectangular shaped island portion 54 which is sized and shaped so as to coapt with an open face of the cassette body 12' (FIGS. 4 and 5).

A peristaltic roller hub assembly 56 (FIGS. 4 and 9) of the pump assembly 50 extends partially through an opening in the island portion 54. Also extendable through an opening in the island portion 54 is a solenoid occluding plunger 58 and a transducer head assembly 60. The roller hub assembly 56, the solenoid plunger 58 and the transducer head assembly 60 cooperate with the fluid cassette 12 for selectively controlling various phases of the supply and removal of fluid to the irrigating and aspirating handpiece during surgery. The island portion 54 has openings which receive the bosses 34.

When mounted the fluid cassette 12 coapts with the island portion 54 and coapts with the hub roller assembly 56 so as to act directly on the aspiration tubing 20 held by the protuberance 46 as shown in FIG. 9. Similarly, the solenoid plunger 58 will compress the irrigation tubing 18 to occlude flow of the irrigation fluid as described below. The transducer head assembly 60 is joined in cooperable relationship with the vacuum control connector 36 so as to monitor and allow control of the vacuum level in the aspiration tubing 20.

With continued reference to FIGS. 4–6, the control unit housing 52 also includes a rigid control or cassette retaining member or door 62. The cassette retaining door 62 is mounted on the front of the control unit housing 52 and is sized and shaped so as to coapt snuggly with the fluid cassette 12 when the latter is mounted on the island portion 54. The relatively rigid nature of the cassette retaining door 62 provides reaction surfaces for the hub roller assembly 56 and the plunger 58. In this embodiment, the cassette retaining door 62 is made of, for example, a clear polycarbonate material which is relatively rigid in comparison with the thin-walled and flexible thermoformed plastic cassette 12. The cassette retaining door 62 is provided with a protuberance 64 (FIG. 9) which is complementary to the recess formed by the protuberance 46 on the fluid cassette 12. Although not necessary, the door 62 can have a recess that receives therein the bottom of recess 40 when the door supports the cassette 12 on the control unit.

As illustrated in FIG. 9, the roller hub assembly 56 includes a plurality of equidistantly and circumferentially spaced roller members 66. The roller hub assembly 56 protrudes slightly beyond the surface of the supporting island 54 so that it can cooperate with an occludable segment 68 of the aspiration tubing. The aspiration tubing segment 48 is removably received in the protuberance 46. Operation of the medical control unit 38 causes the rollers 66 to rotate and in this fashion sequentially compress the occludable segment of the aspiration tubing for effecting the aspiration desired. It is mentioned that the forces required to compress and occlude the aspiration tubing segment 48 would not be provided in the absence of the rigid retaining door 62. It will be appreciated that these rigid portions of the cassette retaining door 62 provide the necessary reaction surfaces so that the rollers 66 can work against the tubing segment 48. Accordingly, the fluid cassette 12 can be made of an inexpensive thermoformed plastic material, for example, which does not require any rigid components. Also, the cassette retaining door 62 is formed with a latch 70 so as to retain the fluid cassette on the island portion 54.

Figure 8A:
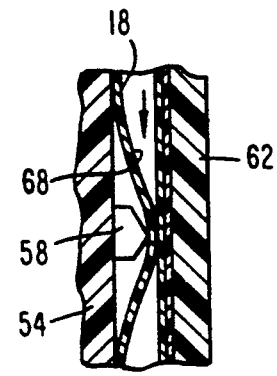
FIGS. 8A and 8B are cross-sectional views illustrating the cooperation between active components of the control unit and irrigation tubing in the fluid cassette in closed and open conditions; respectively, and, FIG. 9 is a cross-sectional view of aspiration type pumping components of the control unit cooperating with the fluid cassette and control unit.
Figure 8B:
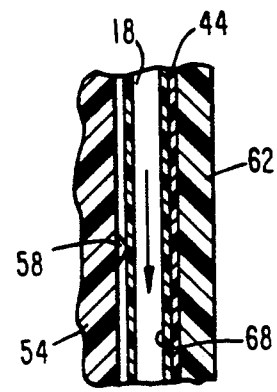

Now referring to FIGS. 8A and 8B, there is shown the operation of the solenoid plunger 58 selectively occluding the irrigation tubing 18 so as to block irrigation fluid to the irrigating and aspirating handpiece. The solenoid plunger 58, as shown in FIG. 8A, is in the closed position, whereby it collapses the irrigation tubing segment 68. The cassette retaining door 62 provides a surface with the necessary rigidity so that the door can perform as a reaction surface to the plunger 58, whereby the irrigation tubing is squeezed to the closed condition. In this regard, the door is structured so as to be positioned immediately juxtaposed the bottom wall 44. Upon opening, the solenoid occluding plunger 58 retracts thereby removing the force opposing the irrigation tubings inherent resiliency and this allows flow of irrigation fluid to the irrigating and aspirating handpiece. It will be appreciated that if the cassette retaining door 62 did not provide the reaction surface necessary, the thin-walled thermoformed plastic cassette 12 would not provide sufficient rigidity to allow occlusion of the irrigation tubing 18. As noted, this is advantageous because the fluid cassette 12 need not be made of rigid material or have portions thereof that are rigid. Instead the cassette assembly can be made of a relatively inexpensive and flexible thermoformed plastic material, such as foamed and unfoamed polystyrene, ABS, PVC, PETG, polyethylene and polypropylene. By way of illustration, the thin-wall cassette construction can have a thickness of about 0.080 inch. Thickness dimensions can vary so long as the cassette functions in the manner noted above. Blow-molded material may be used as well. While the cassette tray could be opaque, a clear resin would enhance placement of the cassette onto the control unit. A pneumatic fluid control approach is envisioned and, therefore, the present invention is, of course, not limited to irrigating and aspirating functions.

After the foregoing detailed description of the construction of the present invention, it is believed that the operation of the fluid cassette and the control unit are easily understood.

Certain changes may be made in the above described system and cassette without departing from the scope from the present invention herein involved. It is intended that all matter contained in this description and shown in the accompanying drawings shall be interpreted as illustrative and not in any limiting sense.

What is claimed is:

1. A medical fluid cassette for use with a medical control unit of the type having an operable assembly for controlling fluid to and from a surgical instrument at an operative site, the control unit having a surface configured to support said cassette and a movable member having at least a relatively rigid portion selectively cooperable with said cassette when said cassette is supported on said control unit surface, said cassette comprising:

a supporting member being made of a flexible material and being sized and shaped to supportingly cooperate with the supporting surface of the control unit; fluid circuitry means positioned to be supported by said supporting member, said circuitry means being controllable by the operable assembly for controlling fluid flow therethrough, such that when said supporting member is supported on the supporting surface, the rigid portion of the movable member forms a reaction surface in cooperating relationship with said fluid circuitry means and the operable assembly can control the flow of fluid through said circuitry means.

2. The medical cassette of claim 1 wherein said supporting member is made of a flexible thermoformed plastic material.

3. The medical cassette of claim 2 wherein said supporting member is sized and shaped to coapt with the supporting surface of the control unit.

4. The medical cassette of claim 3 further comprising holding means for releasably holding said circuitry means in predetermined orientations.

5. The medical cassette of claim 4 wherein said circuitry means comprises tubing segments having flexible occludable portions which are selectively occludable by the operation of respective assemblies of the control unit.

6. The medical cassette of claim 5 further including a sealable cover member which is sealably and removably connected to said supporting member so as to removably cover said supporting member including said tubing segments prior to use thereof.

7. The medical cassette of claim 2 wherein said supporting member has a thin-walled construction.

8. A system comprising: a medical fluid cassette in combination with a medical control unit which controls the flow of fluid to and from a surgical instrument at an operative site, said control unit including a vacuum assembly for aspirating body tissue and fluids from a surgical instrument at an operative site and an irrigating assembly for supplying irrigating fluid to the operative site, a supporting surface configured to support said fluid cassette assembly, and a movable retaining member having rigid means cooperable with said fluid cassette on said supporting surface;

said fluid cassette including a supporting member made of a thin-walled flexible material which is sized and shaped to cooperate with said supporting surface; fluid irrigating and aspirating means for transporting fluids to and from the surgical instrument at the operative site; means for holding said irrigating and aspirating means in cooperable relationship with said vacuum and irrigating assemblies of said control unit, respectively, said cassette when supported on said supporting surface by said retaining member has said rigid means providing a reaction surface so that said irrigating and aspirating assemblies cooperate with said irrigating and aspirating means such that fluid flow therethrough can be controlled by operation of said irrigating and aspirating assemblies.

9. The system of claim 8 wherein said supporting member is made of a flexible thermoformed plastic material.

10. The system of claim 9 wherein said supporting member is sized and shaped to coapt with the supporting surface of said control unit.

11. The system of claim 10 wherein said holding means releasably holds said irrigating and aspirating means in predetermined orientations.

12. The system of claim 11 wherein said irrigating and aspirating means respectively comprises irrigating and aspirating tubing segments with flexible occludable portions which are selectively occludable by the operation of respective irrigating and aspirating assemblies of said control unit.

13. The system assembly of claim 12 further including a sealable cover member which is sealably and removably connected to said supporting member so as to removably cover said supporting member including said irrigating and aspirating tubing segments prior to use thereof.

14. The system of claim 13 wherein said supporting member has a thin walled construction.

15. A medical fluid cassette for use with a medical fluid control unit of the type having a pumping assembly for aspirating fluid from a surgical instrument and an irrigating assembly for controlling flow of irrigation fluid to the surgical instrument, the control unit includes a surface configured to support said fluid cassette and a relatively movable member having rigid means selectively cooperable with said cassette when supported on the supporting surface by the movable member, said cassette comprising:

a supporting member made of a flexible and thin-walled material and being sized and shaped to cooperate with the supporting surface of the control unit;

fluid irrigating and aspirating means being flexible for allowing fluid flow therethrough to be selectively controlled;

means for orienting said irrigating and aspirating means so as to be in cooperable relationship with the pumping and irrigating assemblies of the control unit respectively, said cassette when supported on the supporting surface by the movable member has the rigid means positioned in cooperable relationship to portions of said irrigating and aspirating means so as to provide reaction surfaces for the irrigating and aspirating assemblies when cooperating with said irrigating and aspirating means to control flow of fluid through said irrigating and aspirating means.

* * * * *